United States Patent [19]

Iwasaki et al.

[11] Patent Number: 5,484,593
[45] Date of Patent: Jan. 16, 1996

[54] DIET COMPOSITION COMPRISING GYMNEMA INODRUM AND A METHOD FOR SUPPRESSING THE ABSORPTION OF SACCHARIDES

[76] Inventors: Kazuo Iwasaki, Ota-ku, Tokyo; Chiaki Yamashita, Mitaka-shi, Tokyo; Shahram Mesri, Edogawa-ku, Tokyo; Yoshio Iwasaki, Ota-Ku, Tokyo, all og, Japan

[21] Appl. No.: 705,974

[22] Filed: May 28, 1991

[51] Int. Cl.$^6$ ..................................... A61K 35/78
[52] U.S. Cl. ................ 424/195.1; 514/866; 514/909
[58] Field of Search ................ 424/195.1; 514/909, 514/866

[56] References Cited

U.S. PATENT DOCUMENTS 4,761,286  8/1988  Hiji ........................... 424/195.1
4,912,089  3/1990  Hiji ............................... 514/25

FOREIGN PATENT DOCUMENTS 61-5023    1/1986  Japan .
63-208532  8/1988  Japan .
63-277627  11/1988 Japan .
64-2552    1/1989  Japan .
0138026    2/1989  Japan .
64-38026   2/1989  Japan .
1-102028   4/1989  Japan .
1-120263   5/1989  Japan .

OTHER PUBLICATIONS

Steinmetz E. F. Codex Vegetabilis 1957 #533 Amsterdam Netherlands

*Primary Examiner*—Michael G. Wityshyn
*Assistant Examiner*—Ralph G. Gitomer
*Attorney, Agent, or Firm*—Lowe, Price, Leblanc & Becker

[57] ABSTRACT

A composition for suppressing the absorption of saccharides comprises a *Gymnema inodrum* extract. The extract is prepared by drying and then roasting the leaves of the *Gymnema inodrum* or by subjecting the leaves of *Gymnema inodrum* to extraction with hot water or an alcohol and condensing the extract.

5 Claims, 2 Drawing Sheets

DIET COMPOSITION COMPRISING GYMNEMA INODRUM AND A METHOD FOR SUPPRESSING THE ABSORPTION OF SACCHARIDES

BACKGROUND OF THE INVENTION

The present invention relates to a diet for suppressing the absorption of saccharides from the intestines.

As it is called an age of satiation, in recent years, people have come to enjoy the table full of variety and delicacies, and while the intake of sugars, starches, and the like becomes excessive, the quantity of people's exercise has decreased, so that people have become corpulent from their early childhood and are susceptible to various geriatric diseases such as diabetes mellitus.

As means of preventing one from having corpulence that will induce geriatric diseases, diet therapies wherein the intake of starches and the like is restricted are followed, but these therapies are tiresome and require one's strong determination. Therefore, artificial sweetenings that are not absorbed into the intestines have been developed and used, but these only decrease the amount of sugars and have no relation with the absorption of saccharides originated from carbohydrates, so that they do not provide a complete solution.

To cure a diabetic, a method wherein insulin is administered to suppress the increase in blood sugar has been practiced. Also a method wherein various pharmaceutics are administered to accelerate the secretion of insulin from cells or Langerhans's islands of the pancreas has been practiced. However, these methods are accompanied by diet restriction so that the diabetic is forced to have dull food for a long period of time.

Therefore, diets that comprise, as raw material, *Gymnema sylvestre* produced in India, having an effect for suppressing the absorption of saccharides and intended for the prevention of corpulence and for the suppression of the increase of blood sugar, have been suggested, for example, in Japanese Patent Application Laid-Open Nos. 5023/1986 and 208532/1988.

However since the leaf and extract of *Gymnema sylvestre* are strong in bitterness and astringency and act on the sweetness receptor of taste cells in the mouth, thereby exhibiting a sweetness sensation suppressing effect that prevents the combination of a sweetener with the sweetness receptor, the commercialization using Gymnema requires various measures.

For instance, *Gymnema sylvestre* can be used as an oral food only by reducing or preventing the bitterness, the astringency, or the sweetness sensation suppressing effect through many troublesome processes, for example, by causing an enzyme to act on the *Gymnema sylvestre* in the presence of a farinaceous substance to reduce the bitterness (Japanese Patent Application Laid-Open Nos. 2552/1989 and 102028/1989), by adding a cyclodextrin to the extract thereby enclosing it (Japanese Patent Application Laid-Open No. 120263/1989), by adding a fat-soluble compound (Japanese Patent Application Laid-Open No. 27327/1988), or by coating with a polymeric substance (Japanese Patent Application Laid-Open No. 38026/1989).

SUMMARY OF THE INVENTION

The object of the present invention is to provide a diet for suppressing the absorption of saccharides which is free from unpleasant tastes such as bitterness and astringency, has barely exhibits a sweetness sensation suppressing effect, which suppresses the absorption of saccharides through the intestines, and which can be prepared without requiring troublesome processing.

The inventors have continued research to solve the above problems, have tested and studied Gymnema inodrum, a liana, that grows naturally in the tropics, for example, in Malaysia and Thailand, and have found that the extracted component therefrom is excellent in action for suppressing the absorption of saccharides.

That is, the present invention is directed to a diet for suppressing the absorption of saccharides whose raw material is *Gymnema inodrum* and which is, for example, in a liquid form like tea prepared by drying and roasting the leaves of *Gymnema inodrum* or which is in the form of tablets or granules prepared by subjecting the leaves of *Gymnema inodrum* to extraction with hot water, alcohol or the like, and condensing and drying the extracted component. The tablets or granules will be taken as such or will be added to a food or a drink such as a drinking agent and confectionery.

Since the present diet for suppressing the absorption of saccharides uses, as a raw material, *Gymnema inodrum* having an effect for suppressing the absorption of saccharides, if one takes it and the same amount of saccharides as conventional, the absorption of saccharides can be small and one can reduce calories without unnaturally restricting his diet.

Further, since Gymnema inodrum, in comparison with *Gymnema sylvestre* having the same effect for suppressing the absorption of saccharides, has no unpleasant tastes such as bitterness and astringency and has almost no sweetness suppressing effect, it does not require troublesome processing such as mixing other components to mitigate bitterness or coating with other substance.

DETAILED DESCRIPTION

After 100 g of dried leaves of *Gymnema inodrum* were soaked and stirred in 1 liter of hot water at 80° C. for 8 hours, the liquid was condensed in a thin-layer evaporator to about 250 ml, so that an extract (GI solution) having a solid content of 5.6 g/100 ml was obtained.

1) Assay of the saccharide absorption suppressing effect

The action of the extracted component of *Gymnema inodrum* on the high $K^+$-induced contraction of the ileal longitudinal muscle of a guinea pig was examined by the Magnus method.

That is, the response of the ileal muscle strip suspended in a Magnus bath at 37° C. to the above extract component was magnified by a transducer and an amplifier and was recorded in a recorder.

Tyrode solution (a modified physiological salt solution: PSS) was bubbled with a gas mixture of 95% $O_2$+5%, maintained at pH of 7.2.

First, the ileal muscle was suspended in 15 ml of PSS, and after one hour of equilibration, the PSS solution was replaced with a high $K^+$ Tyrode solution prepared by adding hyperosmotically 60 mM of potassium chloride (KCl) to PSS so as to contract the muscles as referenced.

After the incubation of about 30 minutes, the high $K^+$ solution was replaced with PSS to relax the muscle. After twice application of the high $K^+$ solution to the muscle, by adding 0.75 ml of a diluted solution of the GI solution under the conditions wherein the muscle is contracted by the high $K^+$ solution and after 120 min, replaced with 11 mM pyruvate solution, the change of the tension was recorded.

Figure 1:
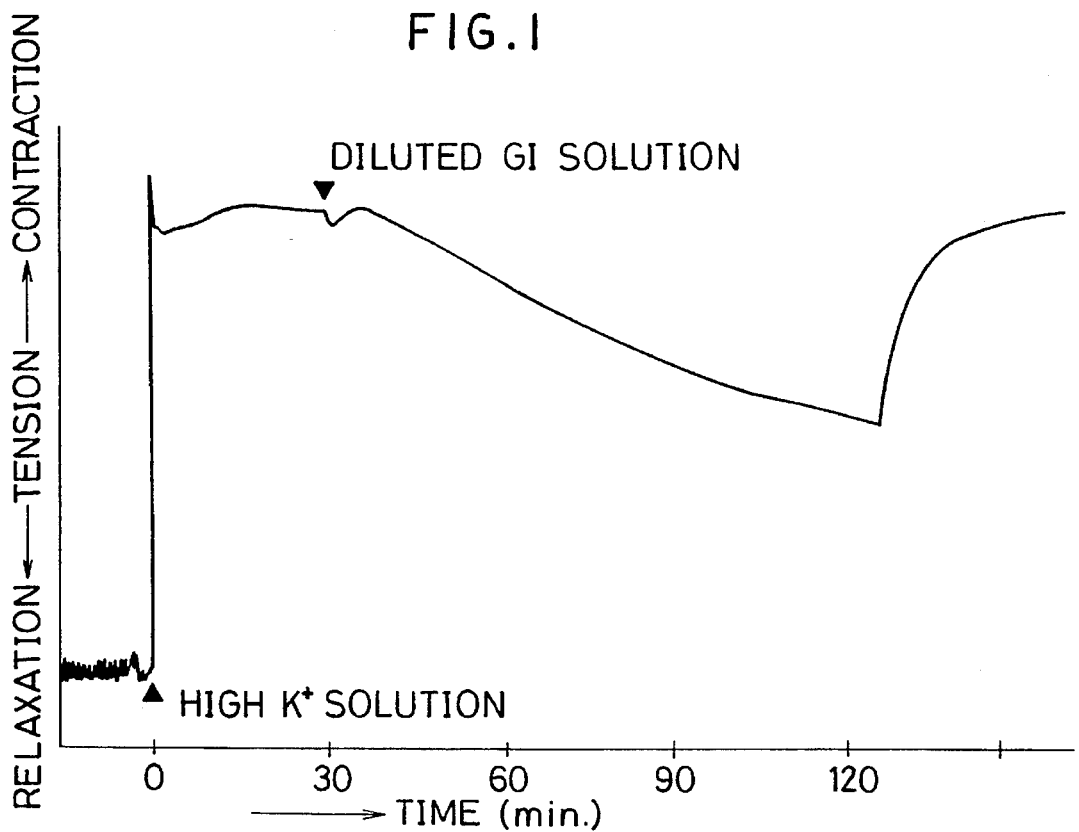
FIG. 1 is a diagram showing an effect of *Gymnema inodrum* extraction on high $K^+$-induced contraction of the ileal longitudinal muscle isolated from guinea pig.

A typical tension change curve of the muscle with 0.75 ml of a 20-time dilute solution of the GI solution is shown in FIG. 1.

Figure 2:
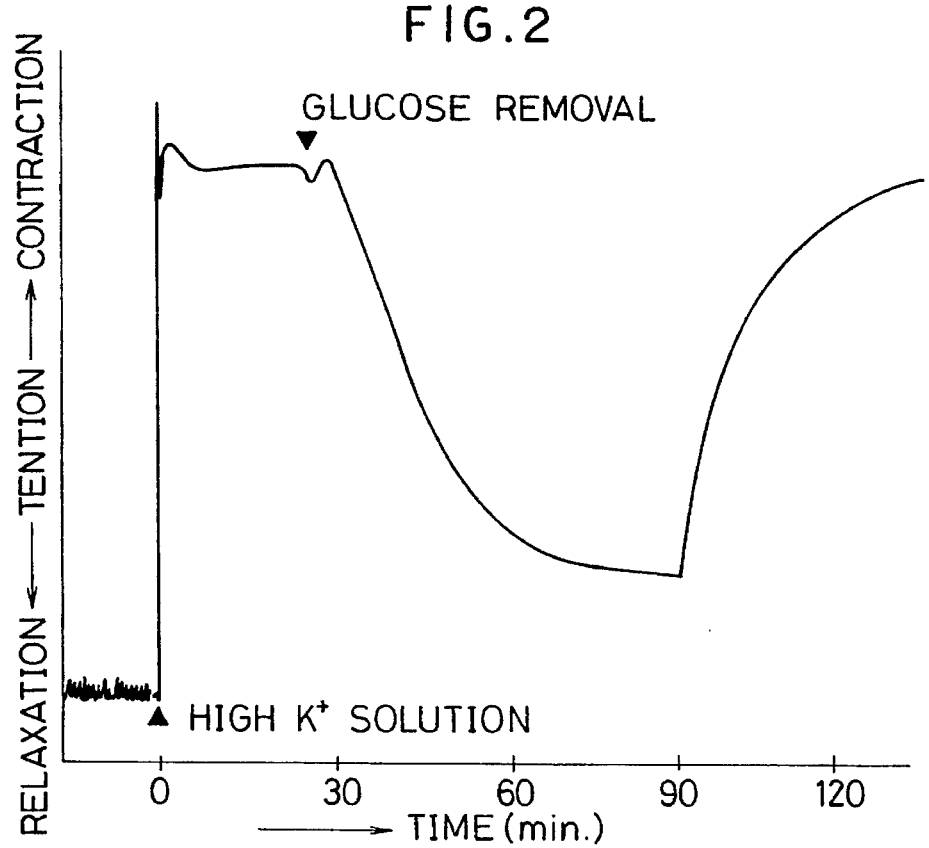
FIG. 2 is a diagram showing a glucose removal on high $K^+$-induced contraction of the ileal longitudinal muscle isolated from guinea pig.

The developed tension by the high $K^+$ solution was decreased when the high $K^+$ Tyrode solution was replaced with a glucose-depleted high $K^+$ solution, and after 90 min. replaced with 11 mM pyruvate solution as is shown in FIG. 2.

As shown in FIG. 1, the muscle relaxed by adding the GI solution. That is, it is assumed that the uptake and/or utilization of glucose is suppressed.

2) Assay of suppressing effect on the blood sugar rise

Figure 3:
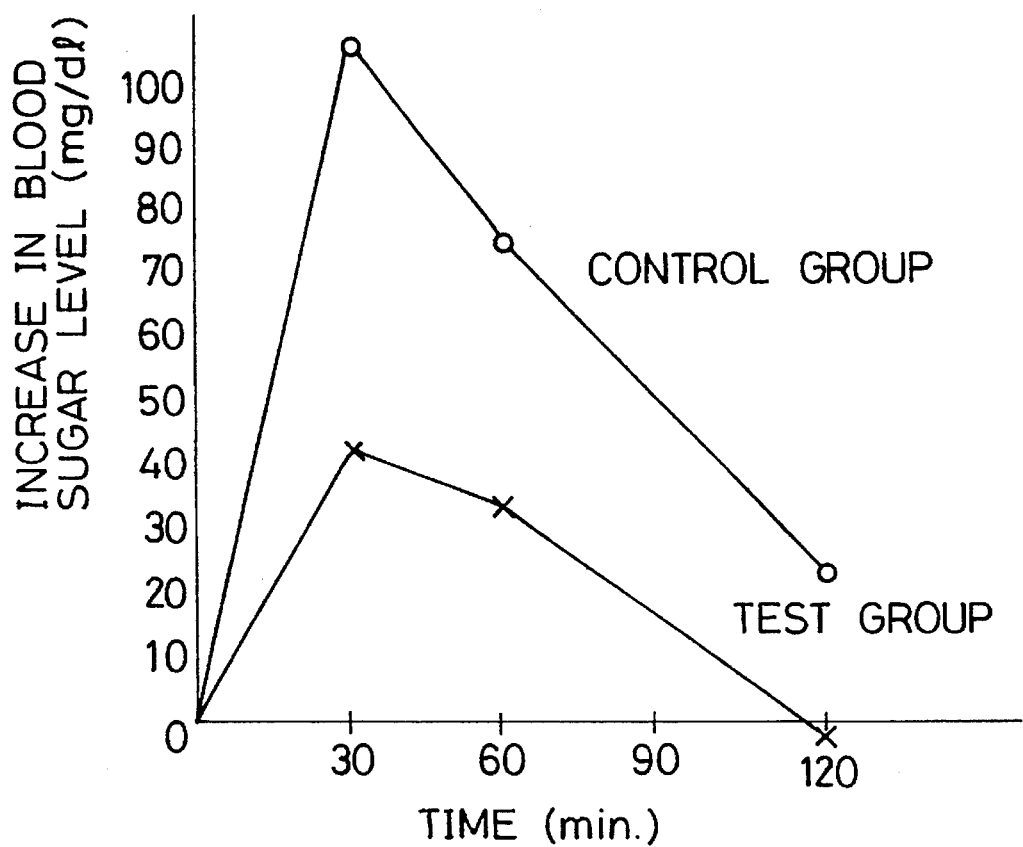
FIG. 3 is a diagram showing a suppressive effect of GI extraction on the blood sugar level with time.

The rise of sugar blood level from the time of the evacuation of the intestines was checked by the oral glucose tolerance test using Wistar-Imamichi-rats (weight: 200 to 300 g) to which was administered dried powder of an extract obtained by freeze-drying the above GI solution. That is, the rats for the test were fasted one night before the test. With respect to a control group of the rats to which only glucose was administered in an amount of 1 g/kg of body weight and a test group of the rats to which glucose in an amount of 1 g/kg of body weight and the above extract component in an amount of 0.1 g/kg of body weight was administered the blood sugar level before the administration and 30 minutes, 60 minutes, and 120 minutes after the administration was determined. The results are shown in FIG. 3. The blood sugar level at the time of the evacuation of the intestines was 96±3 mg/dl.

As indicated in FIG. 3, it is suggested that the extract component of *Gymnema inodrum* suppresses the absorption of glucose and also the rise of blood sugar level.

3) Comparison with Gymnema sylvestre 500 g of each of *Gymnema sylvestre* produced in India and *Gymnema inodrum* produced in Thailand which were prepared by washing the raw leaves with water and drying in the sun were placed in a roaster and were roasted at 200° C. for 15 minutes while rolling the leaves. The leaves were immediately taken out and were allowed to stand to cool to room temperature.

200 ml of hot water was poured to 1 g of each of the two kinds of the roasted leaves, and after they were allowed to stand for 3 minutes, they were filtered through a wire mesh and were subjected to the following organoleptic test.

Test items are odor, bitterness, and sweetness, which were assessed by 10 panelists on a 1–5 scale.

Odor: the peculiar odor when the tea liquid was put in the mouth.

Bitterness: the aftertaste when the tea liquid was swallowed.

Change of sweetness: A commercially available Yokan (sweet jelly of beans) was tasted before and after the drinking of the tea liquid, and the change of the degree of developed bitterness was assessed.

TABLE 1

|  | Odor | Bitterness | Change of sweetness |
| --- | --- | --- | --- |
| Gymnema inodrum | 1 | 1 | 1 |
| Gymnema sylvestre (control) | 5 | 5 | 5 |

As it is clear in Table 1, in comparison with the tea liquid of *Gymnema sylvestre*, that of *Gymnema inodrum* is almost free from peculiarity, so that it is very advantageous to use the *Gymnema inodrum* in various uses.

What is claimed is:

1. A diet composition for suppressing the absorption of saccharides comprising a sugar in humans and animals having intestines, comprising an extract of Gymnema inodrum obtained by subjecting leaves of *Gymnema inodrum* to extraction with water or an alcohol, the extract being included in an amount sufficient to suppress absorption of said saccharides in a human or animal having intestines.

2. A diet composition as defined by claim 1, wherein the extract is obtained from dry, roasted leaves of *Gymnema inodrum*.

3. A diet composition as defined by claim 1, wherein the extract is prepared by subjecting leaves of *Gymnema inodrum* to extraction with water and condensing the resulting liquid.

4. A diet composition as defined by claim 1, wherein the extract is prepared by subjecting leaves of *Gymnema inodrum* to extraction with an alcohol and condensing the resulting liquid.

5. A diet composition comprising an extract of *Gymnema inodrum* obtained by subjecting leaves of *Gymnema inodrum* to extraction with water or an alcohol.

\* \* \* \* \*